United States Patent
Yoshikawa et al.

(10) Patent No.: US 10,563,018 B2
(45) Date of Patent: *Feb. 18, 2020

(54) TITANIUM OXIDE AEROGEL PARTICLE, PHOTOCATALYST-FORMING COMPOSITION, AND PHOTOCATALYST

(71) Applicant: FUJI XEROX CO., LTD., Tokyo (JP)

(72) Inventors: Hideaki Yoshikawa, Kanagawa (JP); Hiroyoshi Okuno, Kanagawa (JP); Yasunobu Kashima, Kanagawa (JP); Takeshi Iwanaga, Kanagawa (JP); Sakae Takeuchi, Kanagawa (JP); Yuka Zenitani, Kanagawa (JP); Shunsuke Nozaki, Kanagawa (JP); Yasuo Kadokura, Kanagawa (JP)

(73) Assignee: FUJI XEROX CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/908,219

(22) Filed: Feb. 28, 2018

(65) Prior Publication Data

US 2019/0077922 A1 Mar. 14, 2019

(30) Foreign Application Priority Data

Sep. 8, 2017 (JP) .................. 2017-173387

(51) Int. Cl.
*C08G 79/00* (2006.01)
*C01G 23/08* (2006.01)
(Continued)

(52) U.S. Cl.
CPC .............. *C08G 79/00* (2013.01); *C01G 23/08* (2013.01); *C07F 7/28* (2013.01); *C08J 3/075* (2013.01);
(Continued)

(58) Field of Classification Search
CPC .. C08G 79/00; C01G 23/08; C07F 7/28; C08J 3/075; C08L 85/00
See application file for complete search history.

(56) References Cited

U.S. PATENT DOCUMENTS

| 5,411,761 A | 5/1995 | Inokuchi et al. |
| 5,919,422 A | 7/1999 | Yamanaka et al. |

(Continued)

FOREIGN PATENT DOCUMENTS

| JP | H05-221640 A | 8/1993 |
| JP | 2001-269573 A | 10/2001 |

(Continued)

OTHER PUBLICATIONS

Wei et al (UV-resistanthydrophobic rutile titania aerogels synthesized through a nonalkoxide ambient pressure drying process, J. Mater. Res. vol. 28 No. 3, (2013), pp. 378-384). (Year: 2013).*

(Continued)

*Primary Examiner* — Melvin C. Mayes
*Assistant Examiner* — Michael Forrest
(74) *Attorney, Agent, or Firm* — Oliff PLC

(57) ABSTRACT

A titanium oxide aerogel particle has absorption at wavelengths of 450 nm and 750 nm in a visible absorption spectrum, a surface to which a metal compound containing a metal atom and a hydrocarbon group is bonded via an oxygen atom, a BET specific surface area in a range of 120 $m^2/g$ to 1,000 $m^2/g$, and a value A is in the range of 0.03 to 0.3. The value A is calculated by formula: A={(peak intensity of C—O bond+peak intensity of C═O bond)/(peak intensity of C—C bond+peak intensity of C═C bond)}. In the formula, the peak intensity is a value determined from a C 1s XPS spectrum.

14 Claims, 1 Drawing Sheet

(51) Int. Cl.
*C08J 3/075* (2006.01)
*C07F 7/28* (2006.01)
*C08L 85/00* (2006.01)

(52) U.S. Cl.
CPC ............ C08L 85/00 (2013.01); *C01P 2002/84* (2013.01); *C01P 2002/85* (2013.01); *C01P 2004/45* (2013.01); *C01P 2004/61* (2013.01); *C01P 2004/62* (2013.01); *C08J 2385/00* (2013.01)

(56) References Cited

U.S. PATENT DOCUMENTS

| | | | |
|---|---|---|---|
| 6,235,270 | B1 | 5/2001 | Ishii et al. |
| 6,777,374 | B2 | 8/2004 | Sahle-Demessie et al. |
| 7,090,823 | B1 | 8/2006 | Liu |
| 7,153,808 | B2 | 12/2006 | Iwamoto et al. |
| 7,211,543 | B2 | 5/2007 | Nakabayashi et al. |
| 7,524,793 | B2 | 4/2009 | Orth-Gerber et al. |
| 7,615,512 | B2 | 11/2009 | Orth-Gerber et al. |
| 7,858,553 | B2 | 12/2010 | Scott et al. |
| 7,887,779 | B2 | 2/2011 | Scott et al. |
| 7,959,980 | B2 | 6/2011 | Nakajima et al. |
| 7,998,453 | B2 | 8/2011 | Scott et al. |
| 9,394,623 | B2 | 7/2016 | Grimes et al. |
| 9,604,198 | B2 | 3/2017 | Furudate et al. |
| 9,744,523 | B2 | 8/2017 | Idriss et al. |
| 9,833,776 | B2 | 12/2017 | Furudate et al. |
| 10,155,220 | B2 * | 12/2018 | Kashima ................ B01J 35/004 |
| 10,183,275 | B2 * | 1/2019 | Okuno .................. B01J 21/063 |
| 2004/0248075 | A1 | 12/2004 | Yamaguchi et al. |
| 2005/0227008 | A1 | 10/2005 | Okada et al. |
| 2006/0009351 | A1 | 1/2006 | Iwamoto et al. |
| 2006/0162617 | A1 | 7/2006 | Tanaka et al. |
| 2007/0248831 | A1 | 10/2007 | Nishihara et al. |
| 2008/0112880 | A1 | 5/2008 | Kayama et al. |
| 2008/0261805 | A1 | 10/2008 | Kanehira et al. |
| 2008/0268268 | A1 | 10/2008 | Masaki et al. |
| 2010/0279118 | A1 | 11/2010 | Hempenius |
| 2011/0159109 | A1 | 6/2011 | Lee et al. |
| 2012/0060269 | A1 | 3/2012 | Tong |
| 2012/0083409 | A1 | 4/2012 | Okuyama et al. |
| 2012/0122668 | A1 | 5/2012 | Celiker et al. |
| 2012/0270028 | A1 | 10/2012 | Orth-Gerber et al. |
| 2013/0164444 | A1 | 6/2013 | Tokumitsu et al. |
| 2013/0284209 | A1 | 10/2013 | Kim et al. |
| 2013/0288055 | A1 | 10/2013 | Doshita et al. |
| 2016/0096949 | A1 | 4/2016 | Evans et al. |
| 2017/0218204 | A1 | 8/2017 | Edwards et al. |
| 2017/0252724 | A1 | 9/2017 | Yoshikawa et al. |
| 2017/0252736 | A1 | 9/2017 | Hirose et al. |

FOREIGN PATENT DOCUMENTS

| | | |
|---|---|---|
| JP | 2004-115541 A | 4/2004 |
| JP | 2006-021112 A | 1/2006 |
| JP | 2006-247524 A | 9/2006 |
| JP | 2006-281155 A | 10/2006 |
| JP | 2007-016111 A | 1/2007 |
| JP | 2008-212841 A | 9/2008 |
| JP | 2009-131760 A | 6/2009 |
| JP | 2010-006629 A | 1/2010 |
| JP | 2011-057552 A | 3/2011 |
| JP | 2013-249229 A | 12/2013 |
| JP | 2014-128768 A | 7/2014 |
| JP | 2014-188417 A | 10/2014 |
| JP | 2015-116526 A | 6/2015 |
| JP | 2015-142917 A | 8/2015 |
| JP | 2015-156509 A | 8/2015 |
| JP | 2016-064407 A | 4/2016 |
| JP | 2016-221447 A | 12/2016 |
| JP | 2017-035645 A | 2/2017 |
| WO | 2008/108367 A1 | 9/2008 |

OTHER PUBLICATIONS

Apr. 4, 2019 Office Action issued in U.S. Appl. No. 15/988,439.
Apr. 20, 2018 Office Action issued in U.S. Appl. No. 15/491,030.
Sep. 27, 2017 Office Action issued in U.S. Appl. No. 15/491,030.
U.S. Appl. No. 15/988,439, filed May 24, 2018 in the name of Takeuchi et al.
Mar. 20, 2018 Office Action issued in U.S. Appl. No. 15/679,476.

\* cited by examiner

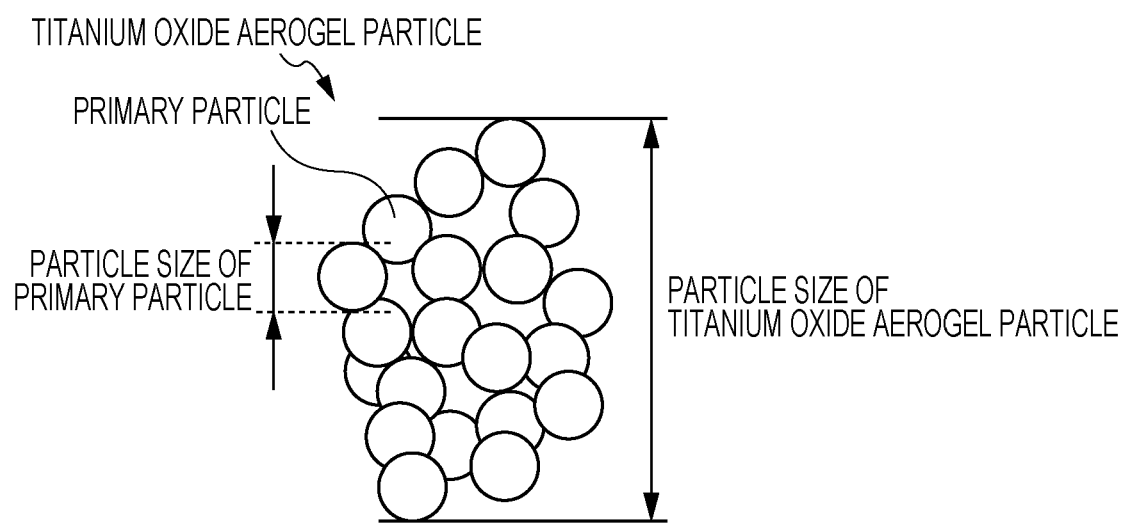

TITANIUM OXIDE AEROGEL PARTICLE, PHOTOCATALYST-FORMING COMPOSITION, AND PHOTOCATALYST

CROSS-REFERENCE TO RELATED APPLICATIONS

This application is based on and claims priority under 35 USC 119 from Japanese Patent Application No. 2017-173387 filed Sep. 8, 2017.

BACKGROUND

Technical Field

The present invention relates to a titanium oxide aerogel particle, a photocatalyst-forming composition, and a photocatalyst.

SUMMARY

According to an aspect of the invention, a titanium oxide aerogel particle is provided. The titanium oxide aerogel particle has absorption at wavelengths of 450 nm and 750 nm in a visible absorption spectrum, a surface to which a metal compound containing a metal atom and a hydrocarbon group is bonded via an oxygen atom, a BET specific surface area in a range of 120 m$^2$/g to 1,000 m$^2$/g, and a value A in the range of 0.03 to 0.3. The value A is calculated by formula: A={(peak intensity of C—O bond+peak intensity of C═O bond)/(peak intensity of C—C bond+peak intensity of C═C bond)}. In the formula, the peak intensity is a value determined from a C 1s XPS spectrum.

BRIEF DESCRIPTION OF THE DRAWING

An exemplary embodiment of the present invention will be described in detail based on the following FIGURE, wherein:

FIGURE is a schematic illustration of a titanium oxide aerogel particle of an exemplary embodiment.

DETAILED DESCRIPTION

Hereinafter, an exemplary embodiment of the invention will be described. Such a description and examples are illustrative of the exemplary embodiment and are not intended to limit the scope of the invention.

In the present disclosure, if there are two or more substances corresponding to one component in a composition, the amount of the component in the composition refers to the total amount of the two or more substances in the composition, unless stated otherwise.

In this disclosure, the term "step" encompasses not only an independent step, but also a step that is not clearly separated from other steps, provided that the desired object of the step is achieved.

XPS is the abbreviation for X-ray photoelectron spectroscopy.

Titanium Oxide Aerogel Particle

A titanium oxide aerogel particle of the exemplary embodiment has a surface to which a metal compound containing a metal atom and a hydrocarbon group is bonded via an oxygen atom satisfies {(peak intensity of C—O bond+peak intensity of C═O bond)/(peak intensity of C—C bond+peak intensity of C═C bond)}=0.03 to 0.3 in a C 1s XPS spectrum and has a BET specific surface area in a range of 120 m$^2$/g to 1,000 m$^2$/g and absorption at wavelengths of 450 nm and 750 nm in a visible absorption spectrum.

The titanium oxide aerogel particle of the exemplary embodiment has an aerogel structure. In the exemplary embodiment, "aerogel" or "aerogel structure" refers to a structure in which primary particles are aggregated while forming a porous structure, and such a structure is a cluster structure formed of aggregated spheroids each having a particle size on the order of nanometers. The internal structures of "aerogel" or "aerogel structure" is a three-dimensional network microstructure.

FIGURE is a schematic illustration of an exemplary structure of the titanium oxide aerogel particle of the exemplary embodiment. The titanium oxide aerogel particle in FIGURE is an aggregate particle in which primary particles aggregate while forming a porous structure.

The titanium oxide aerogel particle of the exemplary embodiment has absorption at wavelengths of 450 nm and 750 nm in a visible absorption spectrum; in other words, the titanium oxide aerogel particle exhibits visible light responsivity, presumably due to the following combined reasons: the titanium oxide aerogel particle has a large surface area with respect to the particle size (in other words, the BET specific surface area is 120 m$^2$/g or more and 1,000 m$^2$/g or less) due to having a porous structure with many pores or voids; an organometallic compound is bonded to the surface of the titanium oxide aerogel particle via an oxygen atom; and the XPS peak intensity ratio of C 1s is 0.03 or more and 0.3 or less. The titanium oxide aerogel particle of the exemplary embodiment has an excellent photocatalytic function presumably because the titanium oxide aerogel particle has not only a large specific surface area, but also a porous structure that improves properties of capturing substances to be degraded.

The titanium oxide aerogel particle of the exemplary embodiment satisfies {(peak intensity of C—O bond+peak intensity of C═O bond)/(peak intensity of C—C bond+peak intensity of C═C bond)}=0.03 to 0.3 in the C 1s XPS spectrum.

In the present disclosure, {(peak intensity of C—O bond+peak intensity of C═O bond)/(peak intensity of C—C bond+peak intensity of C═C bond)} in a C 1s XPS spectrum is referred to as an "XPS peak intensity ratio of C 1s". The XPS peak intensity ratio of C 1s indicates the oxidation degree of the surface of the titanium oxide aerogel particle.

Although the detailed mechanism remains unclear, the surface of the titanium oxide aerogel particle has light absorption at wavelengths of 450 nm and 750 nm presumably due to an organometallic compound that has an appropriately oxidized hydrocarbon group and is present on the surface of the titanium oxide aerogel particle, and as a result, the titanium oxide aerogel particle exhibits a photocatalytic function in the visible range.

If the XPS peak intensity ratio of C 1s is less than 0.03, it is presumable that the hydrocarbon group of the organometallic compound has an excessively low oxidation degree, and the surface of the titanium oxide aerogel particle is unlikely to have absorption in the visible range. If the XPS peak intensity ratio of C 1s is more than 0.3, which indicates that a treatment (e.g., heating treatment) for oxidizing some hydrocarbon groups of the organometallic compound has proceeded too vigorously, and it is presumable that the hydrocarbon groups has been subjected to not only oxidation, but also partial degradation, and as a result, the surface of the titanium oxide aerogel particle has insufficient light absorption in the visible range.

From the foregoing viewpoint, the XPS peak intensity ratio of C 1s of the titanium oxide aerogel particle is preferably 0.03 or more and 0.3 or less, more preferably 0.04 or more and 0.25 or less, and still more preferably 0.05 or more and 0.2 or less.

The XPS peak intensity ratio of C 1s of the titanium oxide aerogel particle is determined from the XPS spectrum. In the C 1s XPS spectrum, multiple peaks appear in accordance with the state of bonding of carbon atoms, and the peaks are each assigned in accordance with their chemical shift positions. In the exemplary embodiment, a peak that appears in the range of 285.5 eV to 287 eV is determined to indicate a peak of a C—O bond, a peak that appears in the range of 287 eV to 288 eV is determined to indicate a peak of a C=O bond, a peak that appears in the range of 284 eV to 285.5 eV is determined to indicate a peak of a C—C bond, and a peak that appears in the range of 284.5 eV to 285 eV is determined to indicate a peak of a C=C bond; however, a peak of a C—O bond and a peak of a C=O bond need not be separate from each other, and a peak of a C—C bond and a peak of a C=C bond need not be separate from each other. (Peak intensity of C—O bond+peak intensity of C=O bond) is determined by using the peak of a C—O bond or the peak of a C=O bond, whichever is higher, and (peak intensity of C—C bond+peak intensity of C=C bond) is determined by using the peak of a C—C bond or the peak of a C=C bond, whichever is higher, thereby determining {(peak intensity of C—O bond+peak intensity of C=O bond)/(peak intensity of C—C bond+peak intensity of C=C bond)}. The measuring method will be fully described below in Examples.

The BET specific surface area of the titanium oxide aerogel particle of the exemplary embodiment is 120 m$^2$/g or more and 1,000 m$^2$/g or less. When the BET specific surface area is 120 m$^2$/g or more, the surface that may adsorb substances to be photodegraded increases relative to the mass, and the titanium oxide aerogel particle readily adsorbs substances to be photodegraded, thereby increasing the photocatalytic function. When the BET specific surface area is 1,000 m$^2$/g or less, the ratio of coarse particles (particles with a particle size of more than 20 μm) decreases, and particle dispersibility is improved in a photocatalyst-forming composition, a photocatalyst, and a structure, which will be described later, and thus a good photocatalytic function is readily exhibited. From the above reasons, in the case where the BET specific surface area of the titanium oxide aerogel particle is set within the above range, a good photocatalytic function is readily exhibited in the visible range.

From the above viewpoint, the BET specific surface area of the titanium oxide aerogel particle is preferably 120 m$^2$/g or more and 1,000 m$^2$/g or less, more preferably 150 m$^2$/g or more 900 m$^2$/g or less, and still more preferably 180 m$^2$/g or more and 800 m$^2$/g or less.

The BET specific surface area of the titanium oxide aerogel particle is determined by the gas adsorption method using nitrogen gas. The measuring method will be fully described below in Examples.

The titanium oxide aerogel particles of the exemplary embodiment preferably have a volume average particle size of 0.1 μm or more and 3 μm or less. When the titanium oxide aerogel particles have a volume average particle size of 0.1 μm or more, the titanium oxide aerogel particle is likely to have a porous structure and to have a larger specific surface area, and thus, the adsorptivity of substances to be photodegraded is likely to improve. Accordingly, a good photocatalytic effect is likely to be exhibited. When the titanium oxide aerogel particles have a volume average particle size of 3 μm or less, the ratio of coarse particles (particles with a particle size of more than 20 μm) decreases, and dispersibility is improved in a photocatalyst-forming composition, a photocatalyst, and a structure, which will be described later, thereby increasing a photocatalytic function. From the above reasons, in the case where the volume average particle size of the titanium oxide aerogel particle is set within the above range, a good photocatalytic function is readily exhibited in the visible range.

From the above viewpoint, the volume average particle size of the titanium oxide aerogel particles is preferably 0.1 μm or more and 3 μm or less, more preferably 0.3 μm or more and 2.8 μm or less, and still more preferably 0.5 μm or more and 2.5 μm or less.

The particle size of the titanium oxide aerogel particle represents the particle size (aggregation size) of an aggregate particle. The volume average particle size of the titanium oxide aerogel particles represents a particle size at which the cumulative volume is 50% from the smaller particle sizes in a volume-based particle size distribution.

The volume particle size distribution of the titanium oxide aerogel particles of the exemplary embodiment is preferably 1.5 or more and 10 or less. When the volume particle size distribution is 1.5 or more, the titanium oxide aerogel particle readily forms a porous structure and has a larger specific surface area, and thus, the absorptivity of substances to be photodegraded readily improves. Accordingly, a good photocatalytic effect is readily exhibited. When the volume particle size distribution is 10 or less, the ratio of coarse particles (particles with a particle size of more than 20 μm) decreases, and dispersibility is improved in a photocatalyst-forming composition, a photocatalyst, and a structure, which will be described later, thereby increasing a photocatalytic function. From the above reasons, in the case where the volume particle size distribution of the titanium oxide aerogel particles is set within the above range, a good photocatalytic function is readily exhibited in the visible range.

From the above viewpoint, the volume particle size distribution of the titanium oxide aerogel particles is preferably 1.5 or more and 10 or less, more preferably 2 or more and 9 or less, and still more preferably 3 or more and 7 or less.

The volume particle size distribution of the titanium oxide aerogel particles of the exemplary embodiment is defined as $(D90v/D10v)^{1/2}$. Here, D90v represents a particle size at which the cumulative volume is 90% from the smaller particle sizes in a volume-based particle size distribution, and D10v represents a particle size at which the cumulative volume is 10% from the smaller particle sizes in a volume-based particle size distribution.

To exhibit a good photocatalytic function in the visible range, the titanium oxide aerogel particle of the exemplary embodiment includes primary particles having an average size (average primary particle size) of 1 nm or more and 120 nm or less. When the average size of the primary particles is 1 nm or more, the aggregate particle has pores with an appropriate size on the surface, thereby improving the adsorptivity of substances to be photodegraded. Accordingly, the titanium oxide aerogel particle readily exhibits a photocatalytic function in the visible range. When the primary particles have an average size of 120 nm or less, primary particles readily aggregate while forming a porous structure, and thus, the aggregate particle readily exhibits a good photocatalytic function in the visible range.

From the above viewpoint, the primary particles preferably have an average size of 1 nm or more and 120 nm or less, more preferably 5 nm or more and 100 nm or less, and still more preferably 10 nm or more and 90 nm or less.

Methods for measuring the volume average particle size and volume particle size distribution of the titanium oxide aerogel particles and for measuring the average size of the primary particles forming the titanium oxide aerogel particle will be described in Examples.

The titanium oxide aerogel particle of the exemplary embodiment has absorption at wavelengths of 450 nm and 750 nm in a visible absorption spectrum.

To exhibit a good photocatalytic function in the visible range, the titanium oxide aerogel particle of the exemplary embodiment preferably has absorption at wavelengths of 450 nm, 600 nm, and 750 nm in a visible absorption spectrum, more preferably over the entire range of 450 nm to 750 nm in a visible absorption spectrum, and particularly preferably over the entire range of 400 nm to 800 nm in a visible absorption spectrum.

To exhibit a good photocatalytic function in a visible range, the titanium oxide aerogel particle of the exemplary embodiment preferably has an absorbance of 0.02 or more at 450 nm (more preferably 0.1 or more, still more preferably 0.2 or more), an absorbance of 0.02 or more at 600 nm (more preferably 0.1 or more, still more preferably 0.2 or more), and an absorbance of 0.02 or more at 750 nm (more preferably 0.1 or more, still more preferably 0.2 or more) in the ultraviolet-visible absorption spectrum with respect to the absorbance at 350 nm taken as 1.

The ultraviolet-visible absorption spectrum of the titanium oxide aerogel particle is determined by measuring a diffuse reflectance spectrum in the range of 200 nm to 900 nm and then obtaining a theoretical absorbance at each wavelength from the diffuse reflectance spectrum by the Kubelka-Munk conversion. A measurement method will be described in detail in Examples below.

The titanium oxide aerogel particle of the exemplary embodiment may be a titanium oxide aerogel particle that is formed by surface treating an untreated titanium oxide aerogel particle with a metal compound containing a metal atom and a hydrocarbon group and then partly oxidizing the hydrocarbon group by heat treatment. In the present disclosure, a titanium oxide aerogel particle that has not been surface treated with an organometallic compound is referred to as an "untreated titanium oxide aerogel particle". In the present disclosure, a metal compound containing a metal atom and a hydrocarbon group is referred to as an "organometallic compound".

Untreated Titanium Oxide Aerogel Particle

The untreated titanium oxide aerogel particle is a titanium oxide aerogel particle that has not been surface treated with an organometallic compound, but may have been subjected to another surface treatment. In the exemplary embodiment, the untreated titanium oxide aerogel particle preferably has not been subjected to any surface treatment including surface treatment with an organometallic compound.

To exhibit a good photocatalytic function, the untreated titanium oxide aerogel particle preferably has a BET specific surface area in the range of 120 $m^2/g$ or more and 1,000 $m^2/g$ or less, more preferably 150 $m^2/g$ or more and 900 $m^2/g$ or less, and still more preferably 180 $m^2/g$ or more and 800 $m^2/g$ or less.

To exhibit a good photocatalytic function, the untreated titanium oxide aerogel particles preferably have a volume average particle size of 0.1 μm or more and 3 μm or less, more preferably 0.3 μm or more and 2.8 μm or less, and still more preferably 0.5 μm or more and 2.5 μm or less.

To exhibit a good photocatalytic function, the untreated titanium oxide aerogel particle is preferably an aggregate particle in which titanium oxide particles (primary particles) aggregate while forming a porous structure. In this case, the titanium oxide particles (primary particles) preferably have an average size of 1 nm or more and 120 nm or less, more preferably 5 nm or more and 100 nm or less, and still more preferably 10 nm or more and 90 nm or less.

A method for producing the untreated titanium oxide aerogel particle is not particularly limited; however, sol-gel processing in which a titanium alkoxide is used as a material is preferably used for confining the range of the BET specific surface area within the above range. The untreated titanium oxide aerogel particle produced by the sol-gel processing is, in a dispersion, a porous particle having a porous structure formed by aggregation of primary particles, and thus, the untreated titanium oxide aerogel particle may have a BET specific surface area within the above range.

The untreated titanium oxide aerogel particle may be made of a hydrolytic condensate of a titanium alkoxide. Some alkoxy groups of the titanium alkoxide may remain unreacted in the particle.

The untreated titanium oxide aerogel particle may include a small amount of a metal element other than titanium, such as silicon or aluminum. When the untreated titanium oxide aerogel particle includes silicon, a silicon content in the range where the element ratio of silicon to titanium, Si/Ti, is 0.05 or less has no influence on the titanium oxide aerogel particle exhibiting a high photocatalyst function in the visible range.

Primary particles included in the untreated titanium oxide aerogel particle may have a single crystal structure of brookite, anatase, or rutile or may have a mixed crystal structure in which such crystals coexist. The crystal structure of the primary particle included in the titanium oxide aerogel particle may be controlled by changing the temperature of heating treatment.

Organometallic Compound

The titanium oxide aerogel particle of the exemplary embodiment has a surface to which an organometallic compound is bonded via an oxygen atom. To readily exhibit visible light responsivity, the organometallic compound preferably includes a metal, carbon, hydrogen, and oxygen atoms alone.

To readily exhibit visible light responsivity, the organometallic compound may be bonded to the surface of the titanium oxide aerogel particle via an oxygen atom O directly bonded to the metal atom M present in the organometallic compound. In other words, the organometallic compound may be bonded to the surface of the titanium oxide aerogel particle by a covalent bond such as M-O—Ti.

To readily exhibit visible light responsivity, the organometallic compound preferably contains a metal atom M and a hydrocarbon group directly bonded to the metal atom M. The organometallic compound preferably is bonded to the surface of the titanium oxide aerogel particle via the oxygen atom O directly bonded to the metal atom M present in the organometallic compound. In other words, to readily exhibit visible light responsivity, the titanium oxide aerogel particle may have, on the surface, a structure in which the hydrocarbon group, the metal atom M, the oxygen atom O, and a titanium atom Ti are bonded by covalent bonding in this order (hydrocarbon group-M-O—Ti).

When the organometallic compound includes plural hydrocarbon groups, at least one hydrocarbon group is preferably bonded directly to the metal atom in the organometallic compound.

The state of interatomic chemical bonding in the organometallic compound may be determined by XPS high resolution analysis (narrow scan analysis).

The metal atom of the organometallic compound is preferably silicon, aluminum, or titanium, more preferably silicon or aluminum, and particularly preferably silicon.

Examples of the hydrocarbon group present in the organometallic compound include saturated or unsaturated aliphatic hydrocarbon groups having 1 to 40 (preferably 1 to 20, more preferably 1 to 18, still more preferably 4 to 12, and further still more preferably 4 to 10) carbon atoms and aromatic hydrocarbon groups having 6 to 27 (preferably 6 to 20, more preferably 6 to 18, still more preferably 6 to 12, and further still more preferably 6 to 10) carbon atoms.

To exhibit a good photocatalytic function and improve dispersibility, the hydrocarbon group present in the organometallic compound is preferably an aliphatic hydrocarbon group, more preferably a saturated aliphatic hydrocarbon group, and particularly preferably an alkyl group. The aliphatic hydrocarbon group may be linear, branched, or cyclic; however, from the viewpoint of dispersibility, a linear or branched aliphatic hydrocarbon group is preferable. The number of carbon atoms in the aliphatic hydrocarbon group is preferably 1 to 20, more preferably 1 to 18, still more preferably 4 to 12, and further still more preferably 4 to 10.

The organometallic compound is particularly preferably a silane compound having a hydrocarbon group. Examples of the silane compound having a hydrocarbon group include chlorosilane compounds, alkoxysilane compounds, and silazane compounds (e.g., hexamethyldisilazane).

To exhibit a good photocatalytic function and improve dispersibility, a silane compound having a hydrocarbon group used in the surface treatment of the titanium oxide aerogel particle is preferably a compound represented by Formula (1): $R^1{}_n SiR^2{}_m$.

In Formula (1), $R^1{}_n SiR^2{}_m$, $R^1$ represents a saturated or unsaturated aliphatic hydrocarbon group having 1 to 20 carbon atoms or an aromatic hydrocarbon group having 6 to 20 carbon atoms; $R^2$ represents a halogen atom or an alkoxy group; n represents an integer of 1 to 3; and m represents an integer of 1 to 3, provided that n+m=4. When n is an integer of 2 or 3, plural $R^1$s may be the same group or different groups. When m is an integer of 2 or 3, plural $R^2$s may be the same group or different groups.

The aliphatic hydrocarbon group represented by $R^1$ may be linear, branched, or cyclic; however, from the viewpoint of dispersibility, a linear or branched aliphatic hydrocarbon group is preferable. To exhibit a good photocatalytic function and improve dispersibility, the number of carbon atoms in the aliphatic hydrocarbon group is preferably 1 to 20, more preferably 1 to 18, still more preferably 4 to 12, and further still more preferably 4 to 10. The aliphatic hydrocarbon group may be saturated or unsaturated; however, to exhibit a good photocatalytic function and improve dispersibility, a saturated aliphatic hydrocarbon group is preferable, and an alkyl group is more preferable.

Examples of the saturated aliphatic hydrocarbon group include linear alkyl groups (e.g., methyl, ethyl, propyl, butyl, pentyl, hexyl, heptyl, octyl, nonyl, decyl, dodecyl, hexadecyl, and icosyl groups), branched alkyl groups (e.g., isopropyl, isobutyl, isopentyl, neopentyl, 2-ethylhexyl, tertiary butyl, tertiary pentyl, and isopentadecyl groups), and cyclic alkyl groups (e.g., cyclopropyl, cyclopentyl, cyclohexyl, cycloheptyl, cyclooctyl, tricyclodecyl, norbornyl, and adamantyl groups).

Examples of the unsaturated aliphatic hydrocarbon group include alkenyl groups (e.g., vinyl (ethenyl), 1-propenyl, 2-propenyl, 2-butenyl, 1-butenyl, 1-hexenyl, 2-dodecenyl, and pentenyl groups) and alkynyl groups (e.g., ethinyl, 1-propynyl, 2-propynyl, 1-butynyl, 3-hexynyl, and 2-dodecynyl groups).

The aliphatic hydrocarbon group may be a substituted aliphatic hydrocarbon group. Examples of the substituent for the aliphatic hydrocarbon group include a halogen atom and epoxy, glycidyl, glycidoxy, mercapto, methacryloyl, and acryloyl groups.

The aromatic hydrocarbon group represented by $R^1$ preferably has 6 to 20 carbon atoms, more preferably 6 to 18 carbon atoms, still more preferably 6 to 12 carbon atoms, and further still more preferably 6 to 10 carbon atoms.

Examples of the aromatic hydrocarbon group include phenylene, biphenylene, terphenylene, naphthalene, and anthracene groups.

The aromatic hydrocarbon group may be a substituted aromatic hydrocarbon group. Examples of the substituent for the aromatic hydrocarbon group include a halogen atom and epoxy, glycidyl, glycidoxy, mercapto, methacryloyl, and acryloyl groups.

Examples of the halogen atom represented by $R^2$ include fluorine, chlorine, bromine, and iodine. Chlorine, bromine, or iodine is preferable as the halogen atom.

The alkoxy group represented by $R^2$ may be an alkoxy group having 1 to 10 (preferably 1 to 8, more preferably 3 to 8) carbon atoms. Examples of the alkoxy group include methoxy, ethoxy, isopropoxy, t-butoxy, n-butoxy, n-hexyloxy, 2-ethylhexyloxy, and 3,5,5-trimethylhexyloxy groups. The alkoxy group may be a substituted alkoxy group. Examples of the substituent for the alkoxy group include a halogen atom and hydroxyl, amino, alkoxy, amide, and carbonyl groups.

To exhibit a good photocatalytic function and improve dispersibility, the compound represented by Formula (1), $R^1{}_n SiR^2{}_m$, is preferably a compound in which $R^1$ is a saturated aliphatic hydrocarbon group. The compound represented by Formula (1), $R^1{}_n SiR^2{}_m$, is particularly preferable, where $R^1$ is a saturated aliphatic hydrocarbon group having 1 to 20 carbon atoms, $R^2$ is a halogen atom or an alkoxy group, n is an integer of 1 to 3, and m is an integer of 1 to 3, provided that n+m=4.

Examples of the compound represented by Formula (1), $R^1{}_n SiR^2{}_m$, include vinyltrimethoxysilane, methyltrimethoxysilane, ethyltrimethoxysilane, propyltrimethoxysilane, butyltrimethoxysilane, hexyltrimethoxysilane, n-octyltrimethoxysilane, decyltrimethoxysilane, dodecyltrimethoxysilane, vinyltriethoxysilane, methyltriethoxysilane, ethyltriethoxysilane, butyltriethoxysilane, hexyltriethoxysilane, decyltriethoxysilane, dodecyltriethoxysilane, phenyltrimethoxysilane, o-methylphenyltrimethoxysilane, p-methylphenyltrimethoxysilane, phenyltriethoxysilane, benzyltriethoxysilane, decyltrichlorosilane, and phenyltrichlorosilane (n=1, m=3);

dimethyldimethoxysilane, dimethyldiethoxysilane, methylvinyldimethoxysilane, methylvinyldiethoxysilane, diphenyldimethoxysilane, diphenyldiethoxysilane, dimethyldichlorosilane, and dichlorodiphenylsilane (n=2, m=2);

trimethylmethoxysilane, trimethylethoxysilane, trimethylchlorosilane, decyldimethylchlorosilane, and triphenylchlorosilane (n=3, m=1); and 3-glycidoxypropyltrimethoxysilane, γ-methacryloxypropyltrimethoxysilane, γ-mercaptopropyltrimethoxysilane, γ-chloropropyltrimethoxysilane, γ-aminopropyltrimethoxysilane, γ-aminopropyltriethoxysilane, γ-(2-aminoethyl)aminopropyltrimethoxysilane, γ-(2-aminoethyl)aminopropylmethyldimethoxysilane, and γ-glycidyloxypropylmethyldimethoxysilane (compounds in which R¹ is a substituted aliphatic hydrocarbon group or a substituted aromatic hydrocarbon group).

Such silane compounds may be used alone or in a combination of two or more.

To exhibit a good photocatalytic function and improve dispersibility, the hydrocarbon group in the silane compound represented by Formula (1) is preferably an aliphatic hydrocarbon group, more preferably a saturated aliphatic hydrocarbon group, and particularly preferably an alkyl group. To exhibit a good photocatalytic function and improve dispersibility, the hydrocarbon group in the silane compound is a saturated aliphatic hydrocarbon group preferably having 1 to 20 carbon atoms, more preferably 1 to 18 carbon atoms, still more preferably 4 to 12 carbon atoms, and particularly preferably 4 to 10 carbon atoms.

Examples of the organometallic compound having aluminum as a metal atom include aluminum chelates, such as di-i-propoxyaluminum.ethyl acetoacetate; and aluminate-based coupling agents, such as acetoalkoxy aluminum diisopropylate.

Examples of the organometallic compound having titanium as a metal atom include titanate-based coupling agents, such as isopropyl triisostearoyl titanate, tetraoctylbis(ditridecylphosphite)titanate, and bis(dioctylpyrophosphate)oxyacetate titanate; and titanium chelates, such as di-i-propoxy bis(ethylacetoacetate)titanium, di-i-propoxy bis(acetylacetonato)titanium, di-i-propoxy bis(triethanolaminato)titanium, di-i-propoxy titanium diacetate, and di-i-propoxy titanium dipropyonate.

Such organometallic compounds may be used alone or in a combination of two or more.

The titanium oxide aerogel particles having a surface to which the organometallic compound is bonded are favored for their good photocatalytic function in the visible range and also favored with respect to the following viewpoints.

The titanium oxide aerogel particles typically have poor dispersibility in a resin or in a solvent. Thus, the coating has poor uniformity, and the photocatalytic function is unlikely to be exhibited.

In contrast, the titanium oxide aerogel particles having a surface to which the organometallic compound is bonded have a hydrocarbon group derived from the organometallic compound and thus have good dispersibility in a resin or in a solvent. This enables formation of a substantially uniform coating, and the titanium oxide aerogel particles are efficiently exposed to light and readily exhibit a photocatalytic function. In addition, aggregation of the titanium oxide aerogel particles or occurrence of coating flaws is suppressed when a paint containing the titanium oxide aerogel particles is applied to surfaces of, for example, an external wall material, a board, a pipe, and unwoven fabric, and thus the photocatalytic function is readily exhibited over a long period.

Method for Producing Titanium Oxide Aerogel Particle

The method for producing the titanium oxide aerogel particles of the exemplary embodiment is not particularly limited. For example, the titanium oxide aerogel particles are obtained by producing porous particles containing titanium oxide by sol-gel processing and surface-treating the porous particles with an organometallic compound. In this case, the surface-treated porous particles are preferably heat-treated to thereby provide the titanium oxide aerogel particles of the exemplary embodiment.

Hereinafter, an exemplary method for producing the titanium oxide aerogel particles of the exemplary embodiment will be described.

The method for producing the titanium oxide aerogel particles of the exemplary embodiment includes at least steps (1), (2), and (3) below, and preferably further includes step (4).

(1) A step of granulating porous particles containing titanium oxide by sol-gel processing and preparing a dispersion containing the porous particles and a solvent (dispersion-preparation step)

(2) A step of removing the solvent from the dispersion by using supercritical carbon dioxide (solvent-removal step)

(3) A step of surface treating the porous particles with a metal compound containing a metal atom and a hydrocarbon group after removing the solvent (surface-treatment step), or preferably, surface treating the porous particles with a metal compound containing a metal atom and a hydrocarbon group in supercritical carbon dioxide after removing the solvent (4) A step of heat treating the porous particles after the surface treatment (heat-treatment step)

(1) Dispersion-Preparation Step

The dispersion-preparation step is a step of, for example, producing titanium oxide by causing a reaction (hydrolysis and condensation) of a titanium alkoxide that is used as a material to prepare a dispersion in which porous particles containing a titanium oxide are dispersed in a solvent.

The dispersion-preparation step is specifically performed as follows.

A titanium alkoxide is added to an alcohol, and an aqueous acid solution is further added dropwise thereto with stirring to produce titanium oxide by the reaction of the titanium alkoxide, thereby preparing a dispersion (porous-particles dispersion) in which porous-particles containing a titanium oxide are dispersed in an alcohol.

The particle sizes of the primary particles and the porous particles may be controlled by an amount of titanium alkoxide added in the dispersion-preparation step. As the amount of titanium alkoxide added increases, the particle size of the primary particles decreases, and the particle size of the porous particles increases. The amount of titanium alkoxide added is preferably 4 parts by mass or more and 65 parts by mass or less, more preferably 10 parts by mass or more and 50 parts by mass or less, relative to 100 parts by mass of the alcohol.

Examples of the titanium alkoxide used in the dispersion-preparation step include tetraalkoxytitaniums, such as tetramethoxytitanium, tetraethoxytitanium, tetrapropoxytitanium, and tetrabutoxytitanium; and alkoxytitanium chelates in which some alkoxy groups are chelated, such as di-i-propoxy bis(ethylacetoacetate)titanium and di-i-propoxy bis(acetylacetonato)titanium. Such compounds may be used alone or in a combination of two or more.

The porous particles may contain a small amount of a metal element other than titanium, such as silicon or aluminum. Examples of a material used to incorporate silicon or aluminum into the porous particles in the dispersion-preparation step include tetraalkoxysilanes, such as tetramethoxysilane, tetraethoxysilane, tetrapropoxysilane, and tetrabutoxysilane; alkyltrialkoxysilanes, such as methyltrimethoxysilane, methyltriethoxysilane, and ethyltriethoxysilane; alkyldialkoxysilanes, such as dimethyldimethoxysilane and dimethyldiethoxysilane; and aluminum alkoxides, such as aluminum isopropoxide. When the silicon element is incorporated in the porous particles, the above materials used in the dispersion-preparation step preferably have an element ratio of silicon to titanium, Si/Ti, in the range of 0 to 0.05.

Examples of the alcohol used in the dispersion-preparation step include methanol, ethanol, propanol, and butanol. Such alcohols may be used alone or in a combination of two or more.

Examples of the acid in the aqueous acid solution used in the dispersion-preparation step include oxalic acid, acetic acid, hydrochloric acid, and nitric acid. The concentration of acid in the aqueous acid solution is preferably 0.001 mass % or more and 1 mass % or less, more preferably 0.005 mass % or more and 0.01 mass % or less.

The amount of the aqueous acid solution added dropwise in the dispersion-preparation step is preferably 0.001 parts by mass or more and 0.1 parts by mass or less relative to 100 parts by mass of the titanium alkoxide.

The porous-particles dispersion obtained in the dispersion-preparation step preferably has a solids concentration of 1 mass % or more and 30 mass % or less.

(2) Solvent-Removal Step

The solvent-removal step is a step of removing a solvent by exposing the dispersion containing the porous particles and the solvent to supercritical carbon dioxide. The solvent-removal treatment with supercritical carbon dioxide is unlikely to cause deformation or clogging of the pores of the porous particles compared with solvent-removal treatment with heat. The use of supercritical carbon dioxide for removing a solvent in the solvent-removal step provides the titanium oxide aerogel particles having a BET specific surface area of 120 $m^2/g$ or more.

The solvent-removal step is specifically performed as follows, for example.

The porous-particle dispersion is placed into a sealed reactor, and then liquefied carbon dioxide is introduced thereinto. Then the sealed reactor is heated while the pressure is increased inside the sealed reactor by using a high-pressure pump, thereby converting the state of the carbon dioxide in the sealed reactor to a supercritical state. Liquefied carbon dioxide is then caused to flow into the sealed reactor to make the supercritical carbon dioxide flow out of the sealed reactor. Accordingly, the supercritical carbon dioxide is caused to flow through the porous-particle dispersion in the sealed reactor. While the supercritical carbon dioxide is flowing in the porous-particles dispersion, the solvent dissolves in the supercritical carbon dioxide and is removed together with the supercritical carbon dioxide flowing out of the gastight reaction container.

The temperature and pressure inside the gastight reaction container are set to a temperature and pressure at which the state of carbon dioxide is converted to a supercritical state. Since the critical point of carbon dioxide is 31.1° C./7.38 MPa, the temperature is set to 50° C. or more and 200° C. or less, and the pressure is set to 10 MPa or more and 30 MPa or less, for example.

(3) Surface-Treatment Step

The surface-treatment step is a step of causing a reaction between a metal compound containing a metal atom and a hydrocarbon group (also referred to as "organometallic compound" in the present disclosure) and the surface of the porous particles. In the surface-treatment step, surface treatment of the porous particles is performed such that a reactive group in the organometallic compound (e.g., a hydrolysable group, such as a halogen group or an alkoxy group) reacts with a reactive group present on the surface of the porous particles (e.g., a hydroxyl group). The surface-treatment step may be performed in air or in an atmosphere of nitrogen. The surface-treatment step performed in supercritical carbon dioxide enables the organometallic compound to reach deep inside the pores of the porous particles, and thus the surface treatment is performed deep inside the pores of the porous particles. Therefore, the surface treatment is preferably performed in supercritical carbon dioxide.

The surface-treatment step is performed by, during stirring, mixing the organometallic compound and the porous particles with each other and causing a reaction therebetween, for example. Otherwise, the surface-treatment step is performed by preparing a treatment liquid by mixing the organometallic compound and the solvent and mixing the porous particles and the treatment liquid with each other while stirring in supercritical carbon dioxide. To retain the porous structure and increase the specific surface area of the porous particles, the organometallic compound is preferably placed in supercritical carbon dioxide continuously after step (2) to cause a reaction between the organometallic compound and the surface of the porous particles in supercritical carbon dioxide.

The temperature and pressure of the surface-treatment step are set to a temperature and pressure at which the state of carbon dioxide is converted to a supercritical state. For example, the surface-treatment step is performed in an atmosphere at a temperature of 50° C. or more and 200° C. or less and at a pressure of 10 MPa or more and 30 MPa or less. The time for stirring is preferably 10 minutes or more and 24 hours or less, more preferably 20 minutes or more and 120 minutes or less, and still more preferably 30 minutes or more and 90 minutes or less.

The organometallic compounds used for the surface treatment are as described above. The organometallic compound may be used alone or in a combination of two or more.

When the treatment liquid prepared by mixing the organometallic compound and a solvent is used, the solvent used for preparing the treatment liquid is not limited, provided that the solvent is a chemical substance compatible with the organometallic compound. Examples of the solvent used to prepare the treatment liquid preferably include alcohols, such as methanol, ethanol, propanol, and butanol; and organic solvents, such as toluene, ethyl acetate, and acetone.

In the treatment liquid, the amount of the organometallic compound is preferably 10 parts by mass or more and 200 parts by mass or less, more preferably 20 parts by mass or more and 180 parts by mass or less, and still more preferably 50 parts by mass or more and 150 parts by mass or less, relative to 100 parts by mass of the solvent.

The amount of the organometallic compound used for the surface treatment is preferably 10 parts by mass or more and 200 parts by mass or less, more preferably 20 parts by mass or more and 180 parts by mass or less, and still more preferably 30 parts by mass or more and 150 parts by mass or less, relative to 100 parts by mass of the porous particles. When the amount of the organometallic compound is 10 parts by mass or more, a good photocatalytic function is readily exhibited in the visible range and dispersibility increases. When the amount of the organometallic compound is 200 parts by mass or less, the excessive increase in the amount of carbon that is derived from the organometallic compound and present on the surface of the porous particles is suppressed, thereby suppressing the deterioration of the photocatalytic function caused by an excess amount of carbon.

After the surface treatment, drying treatment is preferably performed to remove residues, such as excess organometallic compounds and the solvent of the treatment liquid. The drying treatment includes a known treatment, such as spray drying or shelf drying; however, the drying treatment is preferably performed by removing the solvent from the porous-particles dispersion by using supercritical carbon dioxide, more preferably by removing the solvent by dissolving it in supercritical carbon dioxide by flowing supercritical carbon dioxide soon after the surface-treatment step (3). Specifically, these steps may be performed in the same manner as described in step (2).

(4) Heat-Treatment Step

The heat-treatment step further improves the photocatalytic function of the titanium oxide aerogel particle in the visible range. Although the detailed mechanism remains unclear, it is presumed that the heat treatment oxidizes some of the hydrocarbon groups included in the organometallic compound bonded to the surface of the particle, which enables the titanium oxide aerogel particle to have absorption in the visible range and to have a photocharge separation function by absorbing visible light as well as ultraviolet light, and thus the titanium oxide aerogel particle exhibits a photocatalytic function. This indicates that the titanium oxide aerogel particle has absorption at wavelengths of 450 nm and 750 nm in a visible absorption spectrum. In other words, the oxidized hydrocarbon groups present on the surface of the titanium oxide aerogel particle enable absorption of visible light as well as ultra violet light and activate the function of selectively capturing electrons by absorbing. The function decreases the probability of recombination of a positive hole and the electron produced by light absorption and also promotes efficient separation of electric charges, and the promoted separation presumably improves the visible light responsivity of the titanium oxide aerogel particle.

To improve the photocatalytic function, the temperature of the heat treatment is preferably 180° C. or more and 500° C. or less, more preferably 200° C. or more and 450° C. or less, and still more preferably 250° C. or more and 400° C. or less. To improve the photocatalytic function, the time for the heat treatment is preferably 10 minutes or more and 24 hours or less, more preferably 20 minutes or more and 300 minutes or less, and still more preferably 30 minutes or more and 120 minutes or less.

By setting the temperature in the heat treatment to 180° C. or more and 500° C. or less, the titanium oxide aerogel particles that exhibit a good photocatalytic function in the visible range are efficiently obtained. In response to the heat treatment at the temperature of 180° C. or more and 500° C. or less, the hydrocarbon groups that are derived from the organometallic compound and present on the surface of the titanium oxide aerogel particle are likely to be appropriately oxidized, and some C—C bonds or C=C bonds are changed to C—O bonds or C=O bonds.

The heat treatment is preferably performed in an atmosphere in which the oxygen concentration (volume %) is 1% or more and 21% or less. In response to the heat treatment in such an atmosphere of oxygen, the hydrocarbon group that is present on the surface of the titanium oxide aerogel particle and derived from the organometallic compound may be oxidized appropriately and efficiently. The oxygen concentration (volume %) is preferably 3% or more and 21% or less, more preferably 5% or more and 21% or less.

The method for the heat treatment is not particularly limited. The method is a known heating method, such as heating by using an electric furnace, a firing furnace (e.g., a roller hearth kiln or a shuttle kiln), a radiation heating furnace, or a hot plate; or heating by using laser light, infrared rays, ultraviolet rays, or microwaves.

The titanium oxide aerogel particles of the exemplary embodiment may be obtained through the above-described steps.

Photocatalyst-Forming Composition

A photocatalyst-forming composition of the exemplary embodiment includes the titanium oxide aerogel particles of the exemplary embodiment and at least one compound selected from dispersion mediums and binders.

The form of the photocatalyst-forming composition of the exemplary embodiment may be, for example, a dispersion containing a dispersion medium and the titanium oxide aerogel particles of the exemplary embodiment or a composition containing the titanium oxide aerogel particles of the exemplary embodiment and an organic or inorganic binder. The dispersion may be in the form of a paste with high viscosity.

The dispersion medium is preferably water or an organic solvent. Examples of the water include water, distilled water, and pure water. Examples of the organic solvent include, but are not limited to, hydrocarbon-based solvents, ester-based solvents, ether-based solvents, halogen-based solvents, and alcohol-based solvents. From the viewpoint of dispersion stability and storage stability, the dispersion preferably contains at least one compound selected from dispersants and surfactants. The dispersant and the surfactant may be known chemical substances. The dispersion may contain an emulsified binder.

Examples of the binder used for the composition include, but are not limited to, organic binders, such as fluororesins, silicone resins, polyester resins, acrylic resins, styrene resins, acrylonitrile/styrene copolymer resins, acrylonitrile/butadiene/styrene copolymer (ABS) resins, epoxy resins, polycarbonate resins, polyamide resins, polyamine resins, polyurethane resins, polyether resins, polysulfide resins, polyphenol resins, complex resins of the above, and resins obtained by silicone-modifying or halogen-modifying the above resins; and inorganic binders such as glasses, ceramics, and metal powders.

The photocatalyst-forming composition of the exemplary embodiment may contain other components in addition to the above components. The other components are known additives, and examples of the additives include catalytic promoters, coloring agents, fillers, antiseptics, antifoamers, adhesion improvers, and thickeners.

The photocatalyst-forming composition of the exemplary embodiment may include only one type of the titanium oxide aerogel particles of the exemplary embodiment or two or more types.

The content of the titanium oxide aerogel particles of the exemplary embodiment in the photocatalyst-forming composition of the exemplary embodiment is not particularly limited and may be appropriately determined in response to the form, such as a dispersion or a resin composition, and the desired amount of the photocatalyst.

A photocatalyst including the photocatalyst-forming composition of the exemplary embodiment or a structure containing the photocatalyst may be produced by using any known application method. Examples of the method for applying the photocatalyst-forming composition of the exemplary embodiment include spin coating, dip coating, flow coating, spray coating, roll coating, brush coating, sponge coating, screen printing, and ink-jet printing.

Photocatalyst and Structure

The photocatalyst of the exemplary embodiment includes the titanium oxide aerogel particles of the exemplary embodiment or is formed of the titanium oxide aerogel particles of the exemplary embodiment. The structure of the exemplary embodiment includes the titanium oxide aerogel particles of the exemplary embodiment.

The photocatalyst of the exemplary embodiment may be a photocatalyst including the titanium oxide aerogel particles of the exemplary embodiment alone, a photocatalyst obtained by mixing the titanium oxide aerogel particles of the exemplary embodiment and a catalytic promoter with each other, or a photocatalyst obtained by compacting the titanium oxide aerogel particles of the exemplary embodiment into a desired form with an adhesive or an tackifier.

The structure of the exemplary embodiment preferably includes the titanium oxide aerogel particles of the exemplary embodiment as a photocatalyst. From the viewpoint of photocatalytic activity, the structure of the exemplary embodiment includes, at least on the surface, the titanium oxide aerogel particles of the exemplary embodiment.

The structure of the exemplary embodiment is preferably a structure including the titanium oxide aerogel particles of the exemplary embodiment on at least part of the surface of the base material or a structure in which the photocatalyst-forming composition of the exemplary embodiment is applied to at least part of the surface of the base material. In the structure, the amount of the photocatalyst-forming composition of the exemplary embodiment applied is not particularly limited and may be selected as desired.

In the structure of the exemplary embodiment, the titanium oxide aerogel particles of the exemplary embodiment may be attached or fixed to the surface of the base material; however, from the viewpoint of durability of the photocatalyst, the particles are preferably fixed. The fixation method is not particularly limited and is any known fixation method.

Examples of the base material used in the exemplary embodiment include various materials such as inorganic materials or organic materials, and the base material may be of any form. Preferable examples of the base material include metal, ceramic, glass, plastic, rubber, stone, cement, concrete, fibers, cloths, wood, paper, combinations of the above, stacks of the above, and articles that are formed of the above and have at least one coating film on the surface. Preferable examples of the base material from the viewpoint of application include construction materials, exterior materials, window frames, window panes, mirrors, tables, tableware, curtains, lenses, prisms, exteriors and coatings of vehicles, exteriors of machines, exteriors of products, dust-proof covers and coatings, traffic signs, various displays, advertising columns, noise barriers for roadways, noise barriers for railways, bridges, exteriors and coatings of guardrails, interiors and coatings of tunnels, insulators, solar cell covers, solar collector covers, polymer films, polymer sheets, filters, indoor signboards, outdoor signboards, vehicle light covers, outdoor lighting fixtures, air purifiers, water purifiers, medical tools, and nursing care items.

EXAMPLES

Hereinafter the exemplary embodiment of the present invention will be described in detail with reference to examples. The exemplary embodiment of the present invention is not limited to the examples. Hereinafter, all "parts" are by mass unless stated otherwise.

Example 1

Dispersion-Preparation Step 115.4 parts methanol and 14.3 parts tetrabutoxytitanium are put into a reaction container and mixed with each other. While stirring the mixed solution by using a magnetic stirrer at 100 rpm, 7.5 parts of a 0.009 mass % aqueous oxalic acid solution is added dropwise thereto over 30 seconds. The resulting solution is held for 30 minutes while being stirred to obtain 137.2 parts of a dispersion (1) (solid: 3.4 parts; liquid: 133.9 parts).

Solvent-Removal Step 137.2 parts of the dispersion (1) is put into a reaction vessel, and $CO_2$ is supplied thereinto with stirring at 85 rpm. The temperature is raised to 150° C. and the pressure of the vessel is increased to 20 MPa. While continuing stirring, $CO_2$ is flowed in and out to remove 132 parts of the liquid phase over 60 minutes.

Surface-Treatment Step

To the solid phase that remains after the removal of the liquid phase, a mixture of 3.4 parts isobutyltrimethoxysilane and 3.4 parts methanol is added over 5 minutes. The resulting mixture is held at 150° C. and 20 MPa for 30 minutes with stirring at 85 rpm. While continuing stirring, $CO_2$ is flowed in and out to remove 6.5 parts of the liquid phase over 30 minutes. The pressure is decreased to atmospheric pressure over 30 minutes, and 4.0 parts of powder is collected.

Heat-Treatment Step

Into a stainless steel container, 0.5 parts of the powder is weighed. The heat treatment is performed at 380° C. for 60 minutes in an electric furnace in which the oxygen concentration (volume %) is set to 20%. The container is cooling to 30° C., and 0.5 parts of the powder (titanium oxide aerogel particles) is collected.

Comparative Examples 1 to 7 and Examples 2 to 21

Titanium oxide aerogel particles are produced in the same manner as in Example 1 except that materials and treatment conditions are changed as shown in Table 1.

Measurement of Physical Properties of Titanium Oxide Aerogel Particles

The physical properties of titanium oxide aerogel particles obtained in Examples and Comparative Examples are measured by measuring methods described below. Table 2 shows the results. The term "UV-Vis properties" in Table 2 indicates the absorbances at wavelengths of 450 nm, 600 nm, and 750 nm relative to the absorbance at 350 nm taken as 1.

XPS Peak Intensity Ratio

To remove residual $CO_2$ from the pores of the titanium oxide aerogel particles after the supercritical $CO_2$ treatment, degas treatment is performed at a temperature of 25° C. and a reduced pressure of 133 Pa for 3 hours by using a vacuum dry oven (VOS-450VD manufactured by Tokyo Rikakikai Co., LTD.).

Next, the C 1s XPS spectrum is measured under the following conditions by using an XPS analyzer, and {(peak intensity of C—O bond+peak intensity of C=O bond)/(peak intensity of C—C bond+peak intensity of C=C bond)} is determined.

XPS analyzer: VERSA PROBEII manufactured by ULVAC-PHI, Inc.

X ray source: monochromatic AlKα radiation

Output: 25 W

Acceleration voltage: 15 kV

X-ray beam diameter: 100 μm

Signal takeoff angle: 45°

Pass energy: 23.5 eV

Charge neutralization gun 1.0 V/ion gun 10 V

BET Specific Surface Area

A 50-mg sample is pretreated at 30° C. for 120 minutes to be degassed, and a BET specific surface area is determined by a BET multipoint method using nitrogen gas with a purity of 99.99% or more by using a MACSORB HM model-1201 manufactured by Mountech Co., Ltd. as a specific surface area measurement apparatus.

Average Size of Primary Particles (Average Primary Particle Size)

One hundred parts of resin particles having a volume average particle size of 8 μm (styrene-butyl acrylate copolymer particles; copolymerization ratio (mass ratio), 80:20; weight average molecular weight, 130,000; and glass transition temperature, 59° C.) and 1.0 parts of the titanium oxide aerogel particles are mixed with each other at 13,000 rpm for 2 minutes by using a sample mill (SK-M2, manufactured by Kyoritsu-riko Co., Ltd.).

The titanium oxide aerogel particles dispersed in the resin particles are observed under a scanning electron microscope (S-4100 manufactured by Hitachi, Ltd) and images are photographed. When the images are photographed, the scanning electron microscope is adjusted to a magnification that enables image analysis of primary particles, which are particles forming an aggregate particle as shown schematically in FIGURE. The photographed images are loaded into an image analyzer (LUZEX III manufactured by NIRECO CORPORATION), and the area of each particle is determined by image analysis of the particles. The equivalent-circle diameters (nm) are calculated from the area, and the equivalent-circle diameters are averaged to determine the average primary particle size (nm) (denoted by "Dp" in Table 2). The average primary particle size is determined by analyzing about 10 to 50 primary particles.

Volume Average Particle Size and Volumetric Particle Size Distribution of Titanium Oxide Aerogel Particles One hundred parts of resin particles having a volume average particle size of 8 μm (styrene-butyl acrylate copolymer particles; copolymerization ratio (mass ratio), 80:20; weight average molecular weight, 130,000; glass transition temperature, 59° C.) and 1.0 parts of the titanium oxide aerogel particles are mixed with each other at 13,000 rpm for 2 minutes by using a sample mill (SK-M2, manufactured by Kyoritsu-riko Co., Ltd.).

The particle mixture in an amount of 0.1 g is placed into a beaker, and 1.5 g of an aqueous surfactant solution obtained by diluting an anionic surfactant (TAYCAPOWER BN2060 manufactured by Tayca Corporation) with ion-exchanged water to a concentration of 12% is added thereto to soak the particle mixture sufficiently. Next, 5 g of pure water is added thereto, and the resultant is dispersed for 30 min by using an ultrasonic disperser. Then, the resin particles are removed by using No. 5C filter paper to obtain a titanium oxide aerogel particle dispersion. The particle size of the particles in the titanium oxide aerogel particle dispersion is measured using a dynamic light scattering particle size measuring apparatus (NANOTRACK UPA-ST, manufactured by MicrotracBEL Corp.) to obtain a volume-based particle size distribution. D50v, which is a particle size at which the cumulative volume is 50% from smaller particle sizes, is determined and defined as a volume average particle size (μm) (denoted by "Da" in Table 2). In addition, D10v, which is a particle size at which the cumulative volume is 10% from smaller particle sizes, and D90v, which is a particle size at which the cumulative volume is 90% from smaller particle sizes, are determined, and a volume particle size distribution expressed as $GSDv=(D90v/D10v)^{1/2}$ is calculated.

Ultraviolet-Visible Absorption Spectrum

After the titanium oxide aerogel particles are dispersed in tetrahydrofuran, the resultant dispersion is applied to a glass substrate and dried at 24° C. in air. A diffuse reflectance spectrum in the range of 200 nm to 900 nm is measured in a diffuse reflectance configuration by using a U-4100 spectrophotometer (manufactured by Hitachi High-Technologies Corporation) under the following conditions: scanning speed, 600 nm; slit width, 2 nm; and sampling interval, 1 nm. The absorbance at each wavelength is theoretically determined from the diffuse reflectance spectrum by Kubelka-Munk conversion to obtain the ultraviolet-visible absorption spectrum.

The titanium oxide aerogel particles of Examples 1 to 21 have absorption over the entire wavelength range of 400 nm to 800 nm.

Property Evaluation of Titanium Oxide Aerogel Particles
Gas Absorptivity and Gas Degradability To determine the activities of the titanium oxide aerogel particles in Examples and Comparative Examples, the gas degradability in response to visible light irradiation and the gas adsorptivity of the titanium oxide aerogel particles are evaluated. The results are shown in Table 2.

The titanium oxide aerogel particles obtained in Examples and Comparative Examples are dispersed in methanol at a solids concentration of 4% by mass. The resultant dispersion in an amount of 0.25 g is applied to a half of a microscope glass plate (area, 10 cm$^2$) and dried sufficiently to prepare a test piece in which the particles are uniformly attached to the surface of the glass plate (half). Two test pieces are prepared for each of the titanium oxide aerogel particles of Examples and Comparative Examples.

Immediately after being prepared, a test piece is placed into a 1-L TEDLAR bag having one cock valve (one test piece per TEDLAR bag). The TEDLAR bag is deflated, sealed, and then stored in the dark with the coated surface facing upward until the property evaluation tests are performed.

The property evaluation tests are performed as follows.

First, all the air remaining in the TEDLAR bag that includes the test piece is removed through the cock valve by using an aspirator, and 800 ml of ammonium gas at a concentration of 100 ppm is injected into the bag. Then, one of the two TEDLAR bags each including one of the two identical test pieces is continuously irradiated with visible light by using a light emitting diode (LED) that emits visible light at a wavelength of 400 nm or more and 800 nm or less (5,500 lx (lux) at the surface of the test piece). The other of the two TEDLAR bags each including one of the two identical test pieces is stored in a lightproof black box for 1 hour.

The ammonia gas concentrations in the TEDLAR bag including a test piece that has been continuously irradiated with visible light for 1 hour and in the TEDLAR bag including a test piece that has been stored in a lightproof black box for 1 hour are measured by using a detector tube (manufactured by GASTEC Corporation). An ammonia-gas-degradability rate $\Delta S$ in response to visible light irradiation and an ammonia gas adsorptivity indicator $\Delta A$ are determined from the following formulas.

$S1$=ammonia gas concentration (ppm) in TEDLAR bag that has been continuously irradiated with visible light for 1 hour $S2$=ammonia gas concentration (ppm) in TEDLAR bag that has been stored in black box for 1 hour Ammonia gas adsorptivity indicator $\Delta A$ (ppm)=100−$S2$ Ammonia gas degradability rate $\Delta S$ (%)=($S2$−$S1$)/$S2$×100

From the above values, gas adsorptivity and gas degradability are evaluated as follows.

Gas Adsorptivity
G1: ΔA≥90, adsorptivity is excellent
G2: 70≤ΔA<90, adsorptivity is good
G3: 50≤ΔA<70, adsorptivity is fair
G4: ΔA<50, adsorptivity is poor Gas Degradability
G1: ΔS≥30, degradability is excellent
G2: 15≤ΔS<30, degradability is good
G3: 5≤ΔS<15, degradability is fair
G4: ΔS<5, degradability is poor Amount of Coarse Particles A sieve with 20-μm openings is provided and accurately weighed to the nearest 0.01 g. The titanium oxide aerogel particles in an amount of 1.00 g are passed through the sieve by suction with a dust collector. In this process, aggregates on the sieve are fragmented by using a brush and passed through the sieve, and solid aggregates that are not fragmented are left on the sieve. From the weights of the sieve (g) before and after the titanium oxide aerogel particles are passed, a coarse particle indicator is calculated by the following formula. Table 2 shows the results.

Coarse particle indicator (%)=(weight of sieve after passing−weight of sieve before passing)/1.00×100

A: Coarse particle indicator is 1% or less.
B: Coarse particle indicator is more than 1% and 5% or less.
C: Coarse particle indicator is more than 5%.

TABLE 1

| | Dispersion preparation | | | | Retention time (min) | Solvent removal Treatment atmosphere | Surface treatment Treatment atmosphere |
|---|---|---|---|---|---|---|---|
| | Alcohol | | Titanium alkoxide | | | | |
| | Type | Amount (parts) | Type | Amount (parts) | | | |
| Example 1 | methanol | 115.4 | tetrabutoxytitanium | 14.3 | 30 | supercritical CO$_2$ | supercritical CO$_2$ |
| Example 2 | methanol | 115.4 | tetrabutoxytitanium | 75 | 30 | supercritical CO$_2$ | supercritical CO$_2$ |
| Example 3 | methanol | 115.4 | tetrabutoxytitanium | 6 | 30 | supercritical CO$_2$ | supercritical CO$_2$ |
| Example 4 | methanol | 115.4 | tetrapropxytitanium | 15 | 30 | supercritical CO$_2$ | supercritical CO$_2$ |
| Example 5 | butanol | 130 | tetrabutoxytitanium | 14.3 | 30 | supercritical CO$_2$ | supercritical CO$_2$ |
| Example 6 | methanol | 115.4 | tetrabutoxytitanium | 15 | 40 | supercritical CO$_2$ | supercritical CO$_2$ |
| Example 7 | methanol | 115.4 | tetrabutoxytitanium | 14.3 | 35 | supercritical CO$_2$ | supercritical CO$_2$ |
| Example 8 | methanol | 115.4 | tetrabutoxytitanium | 14.3 | 30 | supercritical CO$_2$ | supercritical CO$_2$ |
| Example 9 | methanol | 115.4 | tetrabutoxytitanium | 14.3 | 30 | supercritical CO$_2$ | supercritical CO$_2$ |
| Example 10 | methanol | 115.4 | tetrabutoxytitanium | 14.3 | 35 | supercritical CO$_2$ | supercritical CO$_2$ |
| Example 11 | methanol | 115.4 | tetrabutoxytitanium | 14.3 | 30 | supercritical CO$_2$ | supercritical CO$_2$ |
| Example 12 | methanol | 115.4 | tetrabutoxytitanium | 14.3 | 30 | supercritical CO$_2$ | supercritical CO$_2$ |
| Example 13 | methanol | 115.4 | tetrabutoxytitanium | 14.3 | 35 | supercritical CO$_2$ | supercritical CO$_2$ |
| Example 14 | methanol | 115.4 | tetrabutoxytitanium | 14.3 | 30 | supercritical CO$_2$ | supercritical CO$_2$ |
| Example 15 | methanol | 115.4 | tetrabutoxytitanium | 14.3 | 30 | supercritical CO$_2$ | supercritical CO$_2$ |
| Example 16 | methanol | 115.4 | tetrabutoxytitanium | 14.3 | 35 | supercritical CO$_2$ | supercritical CO$_2$ |
| Example 17 | methanol | 115.4 | tetrabutoxytitanium | 14.3 | 35 | supercritical CO$_2$ | supercritical CO$_2$ |
| Example 18 | methanol | 115.4 | tetrabutoxytitanium | 14.3 | 35 | supercritical CO$_2$ | supercritical CO$_2$ |
| Example 19 | methanol | 115.4 | tetrabutoxytitanium | 14.3 | 35 | supercritical CO$_2$ | supercritical CO$_2$ |
| Example 20 | methanol | 115.4 | tetrabutoxytitanium | 14.3 | 35 | supercritical CO$_2$ | supercritical CO$_2$ |
| Example 21 | methanol | 115.4 | tetrabutoxytitanium | 14.3 | 35 | supercritical CO$_2$ | N$_2$ (dry) |
| Comparative Example 1 | methanol | 115.4 | tetrabutoxytitanium | 14.3 | 40 | supercritical CO$_2$ | supercritical CO$_2$ |
| Comparative Example 2 | methanol | 150 | tetrabutoxytitanium | 14.3 | 35 | supercritical CO$_2$ | supercritical CO$_2$ |
| Comparative Example 3 | methanol | 115.4 | tetrabutoxytitanium | 3 | 30 | supercritical CO$_2$ | supercritical CO$_2$ |
| Comparative Example 4 | methanol | 115.4 | tetrabutoxytitanium | 115 | 40 | supercritical CO$_2$ | supercritical CO$_2$ |
| Comparative Example 5 | methanol | 115.4 | tetrabutoxytitanium | 14.3 | 35 | supercritical CO$_2$ | supercritical CO$_2$ |
| Comparative Example 6 | methanol | 115.4 | tetrabutoxytitanium | 14.3 | 40 | supercritical CO$_2$ | — |
| Comparative Example 7 | methanol | 115.4 | tetrabutoxytitanium | 14.3 | 35 | supercritical CO$_2$ | — |

| | Surface treatment | | Heat treatment | | |
|---|---|---|---|---|---|
| | Organometallic compound | | | | Oxygen |
| | Type | Amount (parts) | Temperature (° C.) | Time (min) | concentration (vol %) |
| Example 1 | isobutyltrimethoxysilane | 3.4 | 380 | 60 | 20 |
| Example 2 | isobutyltrimethoxysilane | 3.4 | 390 | 50 | 19 |
| Example 3 | isobutyltrimethoxysilane | 3.4 | 380 | 60 | 20 |
| Example 4 | isobutyltrimethoxysilane | 3.4 | 380 | 60 | 20 |
| Example 5 | isobutyltrimethoxysilane | 3.4 | 360 | 60 | 20 |
| Example 6 | isobutyltrimethoxysilane | 3.4 | 500 | 60 | 20 |
| Example 7 | isobutyltrimethoxysilane | 3.4 | 180 | 60 | 20 |
| Example 8 | hexyltrimethoxysilane | 4.5 | 350 | 60 | 21 |
| Example 9 | decyltrimethoxysilane | 5.2 | 320 | 60 | 21 |
| Example 10 | methyltrimethoxysilane | 3.1 | 350 | 60 | 21 |

TABLE 1-continued

| | | | | | |
|---|---|---|---|---|---|
| Example 11 | dodecyltrimethoxysilane | 5.5 | 300 | 60 | 21 |
| Example 12 | octadecyltrimethoxysilane | 4.8 | 280 | 60 | 21 |
| Example 13 | octyltrichlorosilane | 3.6 | 300 | 60 | 21 |
| Example 14 | phenyltrimethoxysilane | 3.4 | 350 | 60 | 21 |
| Example 15 | dimethoxy(methyl)octylsilane | 3.4 | 360 | 60 | 21 |
| Example 16 | tri-n-hexylchlorosilane | 4.2 | 350 | 60 | 21 |
| Example 17 | n-octyldimethylchlorosilane | 4.5 | 320 | 60 | 21 |
| Example 18 | hexamethyldisilazane | 3.4 | 360 | 60 | 21 |
| Example 19 | isopropyl triisostearoyl titanate | 3.5 | 380 | 60 | 21 |
| Example 20 | acetoalkoxy aluminum diisopropylate | 3.6 | 360 | 60 | 21 |
| Example 21 | isobutyltrimethoxysilane | 3.4 | 380 | 60 | 21 |
| Comparative Example 1 | isobutyltrimethoxysilane | 0.5 | 110 | 60 | 18 |
| Comparative Example 2 | isobutyltrimethoxysilane | 6.0 | 580 | 80 | 18 |
| Comparative Example 3 | isobutyltrimethoxysilane | 2.0 | 350 | 70 | 20 |
| Comparative Example 4 | isobutyltrimethoxysilane | 4.5 | 400 | 60 | 21 |
| Comparative Example 5 | isobutyltrimethoxysilane | 3.0 | — | — | — |
| Comparative Example 6 | — | — | — | — | — |
| Comparative Example 7 | — | — | 400 | 60 | 20 |

TABLE 2

| | Titanium oxide aerogel particles properties | | | | | | | | Properties evaluation | | |
|---|---|---|---|---|---|---|---|---|---|---|---|
| | XPS peak intensity ratio | BET specific surface area (m²/g) | Dp (nm) | Da (μm) | GSDv | UV-Vis properties | | | Gas adsorptivity | Gas degradability | Coarse particles amount |
| | | | | | | 450 nm absorbance | 600 nm absorbance | 750 nm absorbance | | | |
| Example 1 | 0.15 | 450 | 85 | 1.6 | 4.2 | 0.62 | 0.44 | 0.25 | G1 | G1 | A |
| Example 2 | 0.18 | 985 | 18 | 2.1 | 7.0 | 0.58 | 0.41 | 0.30 | G2 | G1 | A |
| Example 3 | 0.11 | 138 | 108 | 0.5 | 3.2 | 0.60 | 0.37 | 0.24 | G2 | G1 | A |
| Example 4 | 0.14 | 400 | 80 | 1.4 | 3.5 | 0.57 | 0.36 | 0.26 | G1 | G1 | A |
| Example 5 | 0.12 | 395 | 78 | 1.7 | 3.0 | 0.58 | 0.37 | 0.27 | G1 | G1 | A |
| Example 6 | 0.29 | 440 | 82 | 1.3 | 4.1 | 0.52 | 0.42 | 0.21 | G2 | G2 | B |
| Example 7 | 0.04 | 470 | 79 | 1.4 | 3.9 | 0.21 | 0.17 | 0.12 | G2 | G2 | A |
| Example 8 | 0.21 | 500 | 82 | 1.5 | 2.8 | 0.59 | 0.33 | 0.24 | G2 | G1 | A |
| Example 9 | 0.23 | 480 | 85 | 1.3 | 2.5 | 0.48 | 0.32 | 0.29 | G2 | G1 | A |
| Example 10 | 0.16 | 510 | 79 | 1.4 | 3.1 | 0.39 | 0.21 | 0.18 | G2 | G2 | A |
| Example 11 | 0.24 | 470 | 80 | 1.5 | 2.9 | 0.38 | 0.20 | 0.15 | G2 | G2 | A |
| Example 12 | 0.26 | 450 | 82 | 1.3 | 3.2 | 0.46 | 0.33 | 0.28 | G2 | G2 | A |
| Example 13 | 0.22 | 400 | 85 | 1.5 | 2.9 | 0.45 | 0.34 | 0.25 | G2 | G2 | A |
| Example 14 | 0.19 | 460 | 80 | 1.6 | 3.2 | 0.51 | 0.31 | 0.23 | G2 | G2 | A |
| Example 15 | 0.17 | 380 | 78 | 1.3 | 3.3 | 0.43 | 0.26 | 0.22 | G2 | G1 | A |
| Example 16 | 0.11 | 440 | 82 | 1.5 | 3.4 | 0.53 | 0.27 | 0.23 | G2 | G1 | A |
| Example 17 | 0.13 | 470 | 80 | 1.4 | 3.1 | 0.49 | 0.27 | 0.18 | G2 | G1 | A |
| Example 18 | 0.09 | 490 | 79 | 1.3 | 3.2 | 0.42 | 0.21 | 0.19 | G2 | G2 | A |
| Example 19 | 0.07 | 370 | 83 | 1.4 | 3.3 | 0.49 | 0.37 | 0.21 | G2 | G1 | A |
| Example 20 | 0.12 | 420 | 80 | 1.5 | 3.1 | 0.51 | 0.36 | 0.27 | G2 | G1 | A |
| Example 21 | 0.14 | 480 | 85 | 1.6 | 3.2 | 0.61 | 0.38 | 0.26 | G2 | G1 | A |
| Comparative Example 1 | 0.01 | 400 | 80 | 1.5 | 4.0 | 0.01 | 0 | 0 | G2 | G4 | A |
| Comparative Example 2 | 0.42 | 350 | 115 | 0.8 | 2.3 | 0.03 | 0.01 | 0 | G3 | G4 | A |
| Comparative Example 3 | 0.29 | 110 | 150 | 0.7 | 1.5 | 0.23 | 0.10 | 0.02 | G4 | G3 | A |
| Comparative Example 4 | 0.31 | 1150 | 15 | 3.7 | 10.6 | 0.55 | 0.32 | 0.20 | G2 | G3 | C |
| Comparative Example 5 | 0.02 | 380 | 83 | 1.7 | 5.0 | 0 | 0 | 0 | G3 | G4 | A |
| Comparative Example 6 | 0 | 400 | 81 | 1.5 | 3.5 | 0 | 0 | 0 | G3 | G4 | A |
| Comparative Example 7 | 0 | 420 | 83 | 1.7 | 3.2 | 0.01 | 0 | 0 | G3 | G4 | A |

The organometallic compounds in Table 1 are described in detail as follows.

Isopropyl triisostearoyl titanate: PLENACT TTS manufactured by Ajinomoto Co., Inc.

Acetoalkoxy aluminum diisopropylate: PLENACT AL-M manufactured by Ajinomoto Co., Inc.

The results of the property evaluation in Table 2 show that the photocatalytic activities in the visible range in Examples are superior to those in Comparative Examples. In addition, in Examples, the amount of coarse particles is reduced, and dispersibility is secured.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. Titanium oxide aerogel particles having:
   absorption at wavelengths of 450 nm and 750 nm in a visible absorption spectrum,
   a BET specific surface area in a range of 120 $m^2$/g to 1,000 $m^2$/g, and
   a value A being calculated by formula below in a range of 0.03 to 0.3:

$$A=\{(\text{peak intensity of C—O bond} + \text{peak intensity of C=O bond})/(\text{peak intensity of C—C bond} + \text{peak intensity of C=C bond})\},$$

wherein the peak intensity is a value determined from a C 1s XPS spectrum, and each of the titanium oxide aerogel particles has a surface to which a metal compound containing a metal atom and a hydrocarbon group is bonded via an oxygen atom.

2. The titanium oxide aerogel particles according to claim 1, wherein the titanium oxide aerogel particles have absorption over an entire wavelength range of 400 nm to 800 nm in a visible absorption spectrum.

3. The titanium oxide aerogel particles according to claim 1, wherein the titanium oxide aerogel particles have a volume average particle size in a range of 0.1 μm to 3 μm and a volume particle size distribution in a range of 1.5 to 10.

4. The titanium oxide aerogel particles according to claim 1, comprising primary particles in each of the titanium oxide aerogel particles, wherein the primary particles have an average size in a range of 1 nm to 120 nm.

5. The titanium oxide aerogel particles according to claim 1, wherein the metal compound has the hydrocarbon group directly bonded to the metal atom.

6. The titanium oxide aerogel particles according to claim 1, wherein the metal atom is a silicon atom.

7. The titanium oxide aerogel particles according to claim 1, wherein the carbon atom is included in a saturated aliphatic hydrocarbon group having 1 to 20 carbon atoms, an unsaturated aliphatic hydrocarbon group having 2 to 20 carbon atoms, or an aromatic hydrocarbon group having 6 to 20 carbon atoms.

8. The titanium oxide aerogel particles according to claim 1, wherein the carbon atom is included in a saturated aliphatic hydrocarbon group having 1 to 20 carbon atoms.

9. The titanium oxide aerogel particles according to claim 1, wherein the carbon atom is included in a saturated aliphatic hydrocarbon group having 4 to 10 carbon atoms.

10. The titanium oxide aerogel particles according to claim 1, wherein the value A calculated by the formula is in a range of 0.04 to 0.25.

11. The titanium oxide aerogel particles according to claim 1, wherein the BET specific surface area is in a range of 150 $m^2$/g to 900 $m^2$/g.

12. The titanium oxide aerogel particles according to claim 1, wherein the volume average particle size of the titanium oxide aerogel particles is in a range of 0.3 μm to 2.8 μm.

13. A photocatalyst-forming composition comprising:
    the titanium oxide aerogel particles according to claim 1, and
    at least one compound selected from the group consisting of a dispersion medium and a binder.

14. A photocatalyst comprising the titanium oxide aerogel particles according to claim 1.

* * * * *